United States Patent
Richard et al.

(10) Patent No.: US 8,092,818 B2
(45) Date of Patent: Jan. 10, 2012

(54) MEDICAL DEVICES HAVING BIOACTIVE SURFACES

(75) Inventors: Robert E. Richard, Wrentham, MA (US); Michael N. Helmus, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1039 days.

(21) Appl. No.: 11/435,799

(22) Filed: May 17, 2006

(65) Prior Publication Data

US 2007/0269480 A1  Nov. 22, 2007

(51) Int. Cl.
*A61F 2/02* (2006.01)
*A61K 9/00* (2006.01)
*A61K 47/32* (2006.01)
*A61K 38/04* (2006.01)
*A61K 38/06* (2006.01)
*A61K 38/08* (2006.01)
*A61K 31/726* (2006.01)

(52) U.S. Cl. ......... 424/422; 424/400; 424/423; 514/8.1; 514/19.1; 514/21.8; 514/21.9; 514/54; 514/56; 514/772.4; 514/772.6

(58) Field of Classification Search .................. None
See application file for complete search history.

(56) References Cited

U.S. PATENT DOCUMENTS

| | | | | |
|---|---|---|---|---|
| 5,945,457 A | * | 8/1999 | Plate et al. | 514/772.1 |
| 6,156,572 A | | 12/2000 | Bellamkonda et al. | 435/395 |
| 2001/0027237 A1 | | 10/2001 | Mayes et al. | 525/326.1 |
| 2002/0107330 A1 | | 8/2002 | Pinchuk et al. | 525/242 |
| 2003/0087111 A1 | | 5/2003 | Hubbell et al. | 428/457 |
| 2003/0118800 A1 | * | 6/2003 | Thomas et al. | 428/215 |
| 2003/0235603 A1 | * | 12/2003 | Schwarz et al. | 424/426 |
| 2004/0224001 A1 | | 11/2004 | Pacetti et al. | |
| 2004/0267354 A1 | * | 12/2004 | Ringeisen et al. | 623/1.42 |
| 2005/0002865 A1 | | 1/2005 | Klaveness et al. | 424/9.52 |
| 2005/0025802 A1 | * | 2/2005 | Richard et al. | 424/423 |
| 2005/0187146 A1 | | 8/2005 | Helmus et al. | 514/8 |
| 2006/0121076 A1 | | 6/2006 | Ranade et al. | 424/422 |
| 2007/0134420 A1 | * | 6/2007 | Koberstein et al. | 427/258 |

OTHER PUBLICATIONS

Stephen Forster and Thomas Plantenberg, "From Self-Organizing Polymers to Nanohybrid and Biomaterials", Angew. Chem. Int. Ed. 2002, 41, p. 688-714.*

Darrell J. Irvine et al., "Nanoscale Clustering of RGD Peptides at Surfaces Using Comb Polymers. 1. Synthesis and Characterization of Comb Thin Films," *Biomacromolecules*, 2001, 2:85-94.

(Continued)

*Primary Examiner* — Ernst Arnold
*Assistant Examiner* — Christopher R Lea
(74) *Attorney, Agent, or Firm* — Mayer & Williams PC; David B. Bonham; Keum J. Park (57) ABSTRACT

According to an aspect of the present invention, medical devices are provided, which contain (a) a substrate and (b) a polymeric region disposed over the substrate which contains at least one block copolymer. The block copolymer, in turn, contains at least two polymer blocks which phase separate into two or more immiscible phase domains within the polymeric region. Moreover, a bioactive species is covalently attached to at least one of the polymer blocks. By attaching the bioactive species selectively to at least one polymer block, self-assembled clusters of the bioactive species are created as the blocks phase separate into immiscible phase domains.

26 Claims, 2 Drawing Sheets

OTHER PUBLICATIONS

L.G. Griffith, "Polymeric Biomaterials," *Acta Materialia*, 2000, 48: 263-277.

Lily Y. Koo et al., "Co-regulation of cell adhesion by nanoscale RGD organization and mechanical stimulus," *Journal of Cell Science*, 2002, 115: 1423-1433.

S. Tosatti et al., "RGD-containing peptide GCRCYCRGDSPG reduces enhancement of osteoblast differentiation by poly(L-lysine)-*graft*-poly(ethylene glycol)-coated titanium surfaces," *Journal of Biomedical Materials Research Part A*, 2004, 68:458-472.

Guanhua Yu et al., "Poly(D,L-Lactic Acid)-Block-(Ligand-Tethered Poly(Ethylene Glycol) Copolymers as Surface Additives for Promoting Chondrocyte Attachment and Growth," *Journal of Biomedical Materials Research Part B: Applied Biomaterials*, 2005, 76B:65-74.

Zheng Fu et al., "Effects of Raf Kinase Inhibitor Protein Expression on Suppression of Prostate Cancer Metastasis," *Journal of the National Cancer Institute*, 2003, 95:878-889.

Darrell J. Irvine et al., "Simulations of Cell-Surface Integrin Binding to Nanoscale-Clustered Adhesion Ligands," *Biophysical Journal*, 2002, 82:120-132.

Matthew Tirrell et al., "The role of surface science in bioengineered materials," *Surface Science*, 2002, 500:61-83.

Stephen P. Massia et al., "An RGD Spacing of 440 nm Is Sufficient for Integrin $\alpha_v\beta_3$-mediated Fibroblast Spreading and 140 nm for Focal Contact and Stress Fiber Formation," *Journal of Cell Biology*, 1991, 114:1089-1100.

Gargi Maheshwari et al., "Cell adhesion and motility depend on nanoscale RGD clustering," *Journal of Cell Science*, 2000, 113:1677-1686.

Lori Holle et al., "In vitro targeted killing of human endothelial cells by co-incubation of human serum and NGR peptide conjugated human albumin protein bearing $\alpha$ (1-3) galactose epitopes," *Oncology Reports*, 2004, 11: 613-616.

Stephanie Vandevondele et al., "RGD-Grafted Poly-L-lysine-graft-(polyethylene glycol) Copolymers Block Non-specific Protein Adsorption While Promoting Cell Adhesion," *Biotechnology and Bioengineering*, 2003, 82:784-790.

Nikin Patel et al., "Spatially controlled cell engineering on biodegradable polymer surfaces," *FASEB Journal*, 1998, 12: 1447-1454.

Vladimir Proks et al., "Biodegradable Copolymers Carrying Cell-Adhesion Peptide Sequences," *Adv Exp Med Biol*, 2003, 534: 191-199.

E. Lieb et al., "Mediating specific cell adhesion to low-adhesive diblock copolymers by instant modification with cyclic RGD peptides," *Biomaterials*, 2005, 26: 2333-2341.

Horng-Ban Lin et al., "Surface properties of RGD-peptide grafted polyurethane block copolymers: Variable take-off angle and cold-stage ESCA studies," *J. Biomater. Sci. Polymer Edn.*, 1993, 4: 183-198.

Horng-Ban Lin et al., "Synthesis of a novel polyurethane co-polymer containing covalently attached RGD peptide," *J. Biomater. Sci. Polymer Edn.*, 1992, 3: 217-227.

M.J. Fasolka et al., "Observed Substrate Topography-Mediated Lateral Patterning of Diblock Copolymer Films," *Physical Review Letters*, 1997, 79: 3018-3021.

Darrell J. Irvine, et al., "Nanoscale Clustering of RGD Peptides at Surfaces Using Comb Polymers. 1. Synthesis and Characterization of Comb Thin Films," Biomacromolecules 2001, 2, 85-94.

J. Hahm, et al., "Defect evolution in ultrathin films of polystyrene-block-polymethylmethacrylate diblock copolymers observed by atomic force microscopy," Journal of Chemical Physics, vol. 109, No. 23, 1998, 10111-10114.

Tadeusz Pakula, et al., "Dynamics and Viscoelastic Effects in Block Copolymers: Real and Simulated Systems," 2000, pp. 123-177, Marcel Dekker, Inc.

Darrel J. Irvine, et al., "Nanoscale Clustering of RGD Peptides at Surfaces Using Comb Polymers. 2. Surface Segregation of Comb Polymers in Polylactide," Biomacromolecules 2001, 2, 545-556.

* cited by examiner

MEDICAL DEVICES HAVING BIOACTIVE SURFACES

FIELD OF THE INVENTION

Various state of the art medical devices consist of a medical device substrate with a bio-stable or biodegradable polymeric coating. Examples include drug eluting coronary stents, currently available from Boston Scientific (TAXUS), Johnson & Johnson (CYPHER) and others. Examples of polymers for use in such devices include polyisobutylene based block copolymers, poly(butyl methacrylate) and poly(vinyl acetate).

Various approaches have been taken to produce polymers in which a bioactive species is bound to the polymer. Such bioactive polymers may be used, for example, to modify the surface of a medical device in order to alter the biological response of the body to the device by influencing cellular interactions.

In addition, it has been found that surface structure can also regulate cellular interactions with the size of the surface features, as well as their spatial distribution, having an influence on biological response. Recent attempts to control the clustering of bioactive peptides such as RGD peptides [SEQ ID NO: 1] have been made using PEG-based comb polymers. D. J. Irvine et al., "Nanoscale Clustering of RGD Peptides at Surfaces Using Comb Polymers. 1. Synthesis and characterization of Comb Thin Films," *Biomacromolecules* 2001, 2, 85-94. The authors claim to have created nano-scale peptide clusters or a size effective to control cell adhesion.

SUMMARY OF THE INVENTION

According to an aspect of the present invention, medical devices are provided, which contain (a) a substrate and (b) a polymeric region disposed over the substrate which contains at least one block copolymer. The block copolymer, in turn, contains at least two polymer blocks which phase separate into two or more immiscible phase domains within the polymeric region. Moreover, a bioactive species is covalently attached to at least one of the polymer blocks.

An advantage of the present invention is that by attaching the bioactive species selectively to at least one polymer block, self-assembled clusters of the bioactive species are created as the blocks phase separate into immiscible phase domains.

Another advantage of the present invention is that implantable or insertable medical devices may be provided, which display enhanced cellular adhesion.

These and other aspects, embodiments and advantages of the present invention will become immediately apparent to those of ordinary skill in the art upon review of the Detailed Description and Claims to follow.

DETAILED DESCRIPTION OF THE INVENTION

As used herein, "polymers" are molecules containing multiple copies (e.g., 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more differing polymer blocks, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units) that forms part or all of a polymer. Blocks can be branched or unbranched. Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution. As used herein, a "chain" is a linear (unbranched) grouping of constitutional units (i.e., a linear block).

According to an aspect of the present invention, polymeric regions are provided which contain at least one block copolymer. The block copolymer contains at least two polymer blocks which phase separate into two or more immiscible phase domains within the polymeric region. Moreover, a bioactive species is attached to at least one of the polymer blocks. By attaching the bioactive species selectively to at least one polymer block, self-assembled clusters of the bioactive species may be created as the blocks phase separate into immiscible phase domains.

The shape, size, and spacing of the phase domains (and thus the shape, size and spacing of the bioactive agent clusters) may be controlled by a number of factors including the processing techniques that are used to form the phase domains, the overall size of the polymer blocks, and the size of the polymer blocks relative to one another (which affects the relative volume of each phase domain), among other factors.

Figure 5:
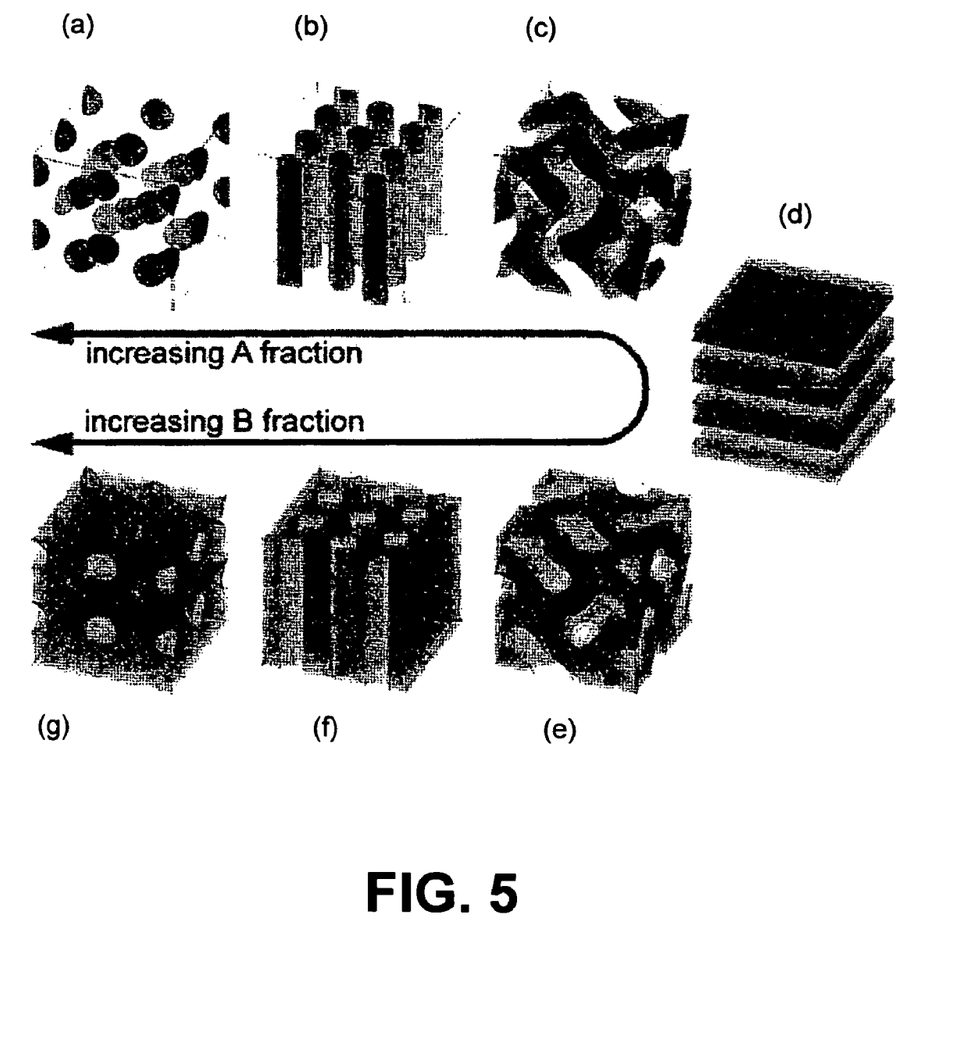
FIG. 5 schematically illustrates idealized morphologies that may be formed for block copolymers two immiscible phases, such as for AB diblock and ABA triblock copolymers.

With respect to the latter factor, the larger the size of one block relative to another, the larger the phase volume created by that block relative to the other. Some typical, albeit idealized, morphologies of block copolymers comprising immiscible polymer blocks A and B (e.g. an AB diblock copolymer, an ABA triblock copolymer, an BAB triblock copolymer, etc.) are illustrated below in FIG. 5. As the fraction of A goes from high to low, the morphologies typically encountered are: (a) spheres of B in a matrix of A (e.g., a body centered cubic lattice), (b) cylinders of B in a matrix of A (e.g., a hexagonal lattice), (c) dual labyrinths of B in a matrix of A (e.g., a double gyroid), otherwise known as a bicontinuous system, (d) alternating sheets of A and B (e.g., lamellae), (e) dual labyrinths of A in a matrix of B, (f) cylinders of A in a matrix of B, and (g) spheres of A in a matrix of B. Note that cylinders and lamellae may be oriented horizontally/parallel with respect to the surface of the polymeric region, vertically/perpendicularly with respect to the surface of the polymeric region, and so forth.

More complex idealized configurations may be exhibited by polymers having three immiscible polymer blocks A, B and C (e.g., an ABC triblock copolymer).

Figure 1:
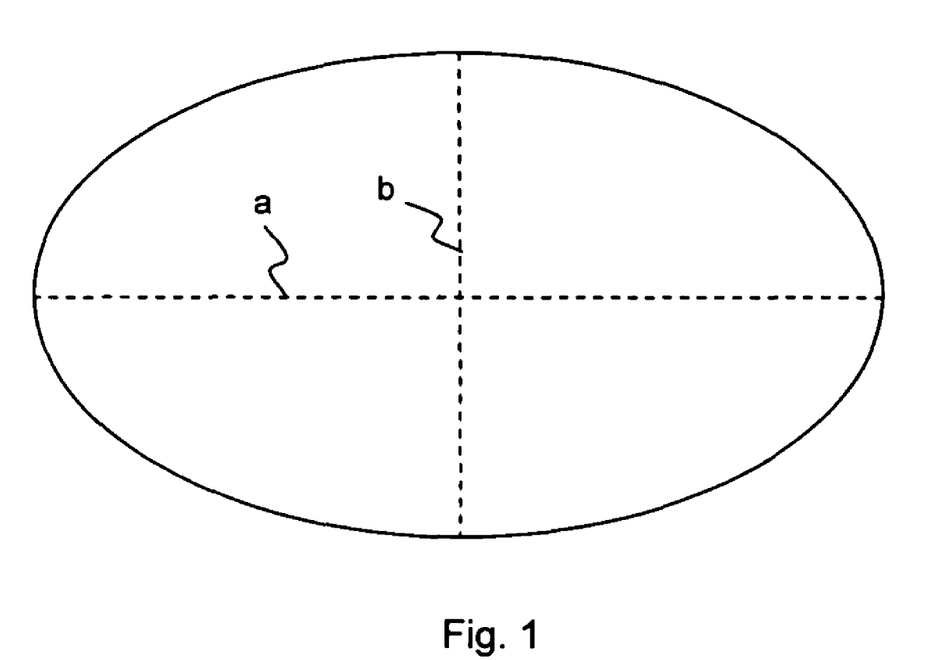
FIG. 1 is a schematic view of an idealized phase domain which is oval in shape at a surface of a polymeric region.
Figure 2:
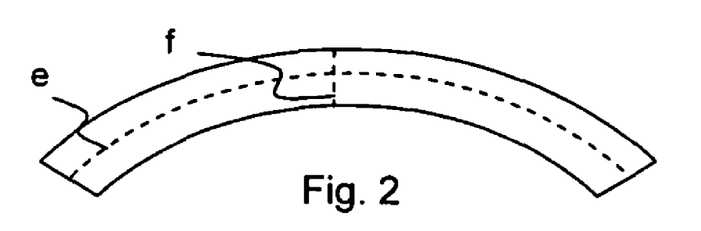
FIGS. 2-4 are schematic views of phase domains of various idealized shapes at a polymeric region surface.
Figure 3:
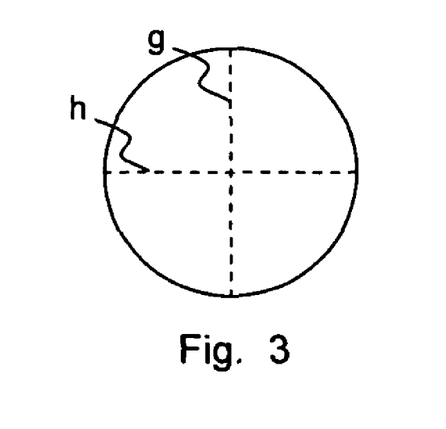
Figure 4:
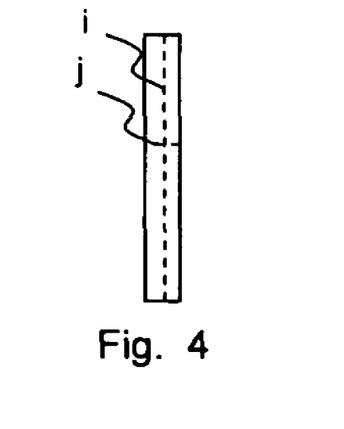

In certain preferred embodiments, the polymeric region is formed under conditions such that at least one of the phase domains has at least one surface dimension that averages between 10 and 500 nm (e.g., from 10 to 25 to 50 to 75 to 100 to 150 to 200 to 300 to 400 to 500 nm). The surface dimensions of a phase domain generally correspond to the length and width of the phase domain at the surface. By way of example, in FIG. 1, lines a and b correspond to the length and width of the surface of the oval phase domain illustrated. In FIG. 2, lines e and f are the surface dimensions (length and width, respectively). In the vertical cylinder of FIG. 3, lines g and h are the surface dimensions (in this case, the length and width are the same and correspond to the diameter). In the vertical lamella of FIG. 4, lines i and j are the surface dimensions (length and width, respectively). Phase domains can be visualized by various techniques known in the block copolymer art, including AFM (atomic force microscopy), TEM (transition electron microscopy) or SEM (scanning electron microscopy), after staining with suitable stain if desired.

In this regard, by controlling the phase separation and by selection of biomolecules that mimic those found on natural surfaces, an optimized surface of selecting the cell type and degree of attachment, spreading and growth may be obtained. An examination of cell surfaces and their cell adhesion integrins show that spacing of these integrins is on the order of tens of nanometers. See, M. Tirrell et al., "The role of surface science in bioengineered materials," *Surface Science* 500 (2002) 61-83 and FIG. 8.37 in R. A. Frietas, Nanomedicine, Landes Bioscience, 1999, pg. 255. For example, a study by S. P. Massia, "An RGD spacing of 440 nm is sufficient for integrin alpha V beta 3-mediated fibroblast spreading and 140 nm for focal contact and stress fiber formation," *The Journal of Cell Biology*, Vol. 114, 1089-1100. 1991, demonstrate that RGD [SEQ ID NO: 1] spacing on a surface ranging between 10 and 440 nm can influence cell attachment and spreading. Others have suggested that integrin clustering may be required to support cell locomotion, with non-clustered integrin ligands (in this case, the YGRGD peptide [SEQ ID NO: 2]) supporting cell attachment, but neither full spreading nor haptokinetic or chemokinetic motility. See G. Maheshwari et al., "Cell adhesion and motility depend on nanoscale RGD clustering," *Journal of Cell Science* 113, 1677-1686 (2000).

As used herein, a "bioactive species" is a material that promotes cell adhesion, for example, bone cells or soft tissue cells, with minimal adverse biological effects (e.g., the formation of connective tissue such as fibrous connective tissue).

Examples of bioactive species suitable for the practice of the present invention include adhesive polysaccharide-containing species and adhesive peptide-containing species (including cell adhesive peptides and full-length proteins) among others. Such species may be selected, for example, from suitable members of the following: (a) extracellular materials such as submucosa, bone marrow, extracellular membrane, and basement membrane, various components of extracellular materials, including fibrous materials and ground substance (e.g., glycosaminoglycans, proteoglycans, and glycoproteins), for instance, collagen, laminin, elastin, fibronectin, heparin sulfate, hyaluron, dermatan sulfate, keratin sulfate, and chrondroitin sulfate, among others; (b) adhesive species such as ankyrins, cadherins (calcium dependent adhesion molecules), N-CAMs (calcium independent adhesive molecules), connexins, immunoglobulins, mucoadhesives, sialyl Lex, plant or bacterial lectins (adhesion molecules which specifically bind to sugar moieties of the epithelial cell membrane), integrins, entactin, fibrin, vimentin, glycolipids, glycophorin, glycoproteins, hyaluronic acid, spektrin, von Willebrand factor, vinculin, vitronectin, and species (including peptides and proteins), which contain cell adhesion peptides such as RGD tripeptide (i.e., Arg-Gly-Asp) [SEQ ID NO: 1], which has been identified to be responsible for some of the cell adhesion properties of fibronectin, laminin, collagen I, collagen IV, thrombospondin, and tenascin), REDV tetrapeptide (i.e., Arg-Glu-Asp-Val) [SEQ ID NO: 3], which has been shown to support endothelial cell adhesion but not that of smooth muscle cells, fibroblasts, or platelets, and YIGSR pentapeptide (i.e., Tyr-Ile-Gly-Ser-Arg) [SEQ ID NO: 4], which promotes epithelial cell attachment, but not platelet adhesion ); and (c) growth factors. More information on RGD [SEQ ID NO: 1], REDV [SEQ ID NO: 3], and YIGSR [SEQ ID NO: 4] peptides can be found in U.S. Pat. No. 6,156,572 and U.S. Patent Publication No. 2003/0087111. A further example of a bioactive species is NGR [SEQ ID NO: 5] tripeptide, which binds to CD13 of endothelial cells. See, e.g., L. Holle et al., "In vitro targeted killing of human endothelial cells by co-incubation of human serum and NGR [SEQ ID NO: 5] peptide conjugated human albumin protein bearing alpha (1-3) galactose epitopes," *Oncol. Rep.* 2004 March; 11 (3):613-6.

In some embodiments, a first polymer block is provided with a first bioactive species (e.g., a species comprising a peptide binding sequence such as an RGD [SEQ ID NO: 1] peptide), while a second immiscible polymer block is provided with a second bioactive species (e.g., a glycosaminoglycan species, such as heparin for thromboresistance or heparin sulfate for biocompatibility). See, e.g., U.S. Patent Publication No. 2005/0187146 to Helmus and Richard, the disclosure of which is incorporated by reference in its entirety, for further examples.

As noted above, block copolymers for use in conjunction with the present invention preferably contain at least two polymer blocks that phase separate into two or more immiscible phase domains.

Moreover, as indicated above, the shape, size and spacing of such immiscible phases can be controlled by controlling the overall size of the polymer blocks, the size of the polymer blocks relative to one another, and the processing techniques that are used to form the phase domains.

For example, the size of the phase domains that are formed may be reduced by reducing the overall size (e.g., the molecular weight) of the polymer blocks, until the point where the polymer blocks are so small that they do not produce recognizably distinct phases, even under microscopy.

As another example, the greater the molecular weight of a first polymer block relative to that of a second polymer block, the greater the volume fraction of the phase corresponding to the first polymer block relative to the volume fraction of the phase corresponding to the second polymer block. By varying the volume fraction of the various phase domains in the fashion, different morphologies may be created (see, e.g., the spherical, cylindrical, lamallar and double gyroid morphologies of FIG. 5, discussed above, among other possibilities).

As another example, the orientation of block copolymers into immiscible phase domains via rapid solidification, including directional solidification and/or epitaxy, have been shown to form various structures, such as vertical lamellae and vertical cylinders, among others. In this way, orientation of phase domain structures may be controlled to be approximately uniform, and spatial arrangement of the domains may be controlled. For further information, see, e.g., U.S. Patent Appln. Pub. No. 2003/0118800 entitled "Large area orientation of block copolymer microdomains in thin films" and the references cited therein. See also U.S. Ser. No. 11/005,852, entitled "Orienting polymer domains for controlled drug delivery," and the references cited therein, in which electric fields, magnetic fields, mechanical shear fields or solvent gradient fields are applied to influence the spatial orientation of the phase separated domains.

Annealing processes may also be employed in conjunction with phase domain formation, particularly those approximating an equilibrium phase domain arrangement.

In some embodiments, the block copolymer employed is biostable, whereas in other embodiments, the block copolymer is biodegradable, whereas in still other embodiments the block copolymer contains at least one biostable block and at least one biodegradable polymer block.

In some embodiments, the block copolymer contains at least one hydrophilic polymer chain and at least one hydrophobic (lipophilic) polymer chain.

In some embodiments, the block copolymer contains at least one low $T_g$ polymer chain and at least one high $T_g$ polymer chain. In general, low $T_g$ polymer chains are soft and elastomeric at room (and body) temperature, whereas high $T_g$ polymer chains are hard. Certain copolymers of this type are known for their combination of high strength and elasticity, making them ideal for use in conjunction with expandable medical devices, among other uses. As used herein, "low $T_g$ polymer chains" are those that display a $T_g$ that is below body temperature, more typically 37° C. to 20° C. to 0° C. to −25° C. to −50° C. or below. Conversely, elevated or "high $T_g$ polymer chains" are those that display a glass transition temperature that is above body temperature, more typically 37° C. to 50° C. to 75° C. to 100° C. or above. $T_g$ can be measured by any of a number of techniques including differential scanning calorimetry (DSC).

Block copolymer configurations may vary widely and include, for example, the following configurations among others (in which polymer chains H and L may designate, for example, high and low $T_g$ polymer chains, respectively, hydrophilic and lipophilic chains, respectively, or biodegradable and biostable chains, respectively): (a) block copolymers having alternating chains of the type $(HL)_m$, $L(HL)_m$ and $H(LH)_m$ where m is a positive whole number of 1 or more, and (b) multiarm copolymers such as $X(LH)_n$, and $X(HL)_n$, where n is a positive whole number of 2 or more, and X is a hub species (e.g., an initiator molecule residue, a residue of a molecule to which preformed polymer chains are attached, etc.). Note that hub species are generally ignored in describing block copolymer morphology, which $X(LH)_2$ being designated as an HLH triblock copolymer.

A wide range of monomers are available for forming the polymer blocks of the block copolymers of the invention.

For instance, specific examples of low $T_g$ polymer blocks include homopolymer and copolymer chains containing one or more of the following (listed along with published $T_g$'s for homopolymers of the same): (1) acrylic monomers including: (a) alkyl acrylates such as methyl acrylate ($T_g$ 10° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) haloalkyl acrylates such as 2,2,2-trifluoroethyl acrylate ($T_g$ −10° C.) and (e) cyano-alkyl acrylates such as 2-cyanoethyl acrylate ($T_g$ 4° C.); (2) methacrylic monomers including (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.); (3) vinyl ether monomers including (a) alkyl vinyl ethers such as ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.); (4) cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.); (5) ester monomers (other than acrylates and methacrylates) including ethylene malonate ($T_g$ −29° C.), vinyl acetate ($T_g$ 30° C.), and vinyl propionate ($T_g$ 10° C.); (6) alkene monomers including ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.); (7) halogenated alkene monomers including vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.); and (8) siloxane monomers including dimethylsiloxane ($T_g$ −127° C.), diethylsiloxane, methylethylsiloxane, methylphenylsiloxane ($T_g$ −86° C.), and diphenylsiloxane.

Specific examples of high $T_g$ polymer blocks include homopolymer and copolymer chains containing one or more of the following: (1) vinyl aromatic monomers including (a) unsubstituted vinyl aromatics, such as styrene ($T_g$ 100° C.) and 2-vinyl naphthalene ($T_g$ 151° C.), (b) vinyl substituted aromatics such as a-methyl styrene, and (c) ring-substituted vinyl aromatics including ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), ring-alkoxylated vinyl aromatics, such as 4-methoxystyrene ($T_g$ 113° C.) and 4-ethoxystyrene ($T_g$ 86° C.), ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and ring-ester-substituted vinyl aromatics such as 4-acetoxystyrene ($T_g$ 116° C.); (2) other vinyl monomers including (a) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (b) vinyl amines such as 2-vinyl pyridine ($T_g$ 104° C.), 4-vinyl pyridine ($T_g$ 142° C.), and vinyl carbazole ($T_g$ 227° C.), (c) vinyl halides such as vinyl chloride ($T_g$ 81° C.) and vinyl fluoride ($T_g$ 40° C.); (d) alkyl vinyl ethers such as tert-butyl vinyl ether ($T_g$ 88° C.) and cyclohexyl vinyl ether ($T_g$ 81° C.), and (e) other vinyl compounds such as vinyl ferrocene ($T_g$ 189° C.); (3) other aromatic monomers including acenaphthalene ($T_g$ 214° C.) and indene ($T_g$ 85° C.); (4) methacrylic monomers including (a) methacrylic acid anhydride ($T_g$ 159° C.), (b) methacrylic acid esters (methacrylates) including (i) alkyl methacrylates such as methyl methacrylate ($T_g$ 105-120° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (c) other methacrylic-acid derivatives including methacrylonitrile ($T_g$ 120° C.); (5) acrylic monomers including (a) certain acrylic acid esters such as tert-butyl acrylate ($T_g$ 43-107° C.), hexyl acrylate ($T_g$ 57° C.) and isobornyl acrylate ($T_g$ 94° C.); and (b) other acrylic-acid derivatives including acrylonitrile ($T_g$ 125° C.).

Further specific examples of high and low $T_g$ polymer chains include biodegradable polymer chains that consist of or contain one or more monomers selected from the following: (a) polyester-forming monomers such as naphthalate and terephthalate esters ($T_g$ 70-80° C. for polyethylene terephthalate), d-lactide, l-lactide ($T_g$ 60-65° C.), glycolic acid ($T_g$ 35-40° C.), epsilon-caprolactone ($T_g$ −65 to −60° C.), hydroxybutyrate, and hydroxyvalerate, (b) monomers that form polyether-esters such as p-dioxanone ($T_g$ −10 to 0° C.), and (c) monomers that form polycarbonates such as ethylene carbonate (1,3-dioxolan-2-one) ($T_g$ 10 to 30° C.), propylene carbonate (4-methyl-1,3-dioxolan-2-one), trimethylene carbonate (1,3-dioxan-2-one), tetramethylene carbonate (1,3-dioxepan-2-one), as well as 1,4-dioxepan-2-one, 1,5-dioxepan-2-one and 6,6-dimethyl-1,4-dioxan-2-one.

The bioactive species may be placed, for example, at the ends of the copolymer chains, or along the length of the copolymer chains. Where placed at ends of the copolymer chains, the bioactive species density may be increased by decreasing the length of the copolymer chains (thereby increasing the number of bioactive species per unit volume), and conversely the bioactive species density may be reduced by increasing the length of the copolymer chains.

Where placed along the length of the copolymer chains, the bioactive species density at the surface may be increased by increasing the number of bioactive species along the chain length (e.g., by increasing the length of the chain or the density of the bioactive species along the chain), and decreased by increased by decreasing the number of bioactive species along the chain length.

With respect to attachment, the bioactive species may be covalently bonded to a monomer prior to polymerization or it may be subsequently attached to the polymer after polymer synthesis, or even after an underlying substrate is been coated with a polymeric region that comprises the polymer.

Polymers that contain functional groups that readily covalently bond to bioactive species include monomers having (a) amine groups (e.g., those formed using aminoalkyl acrylates and methacrylates such as 2-aminoethyl methacrylate), 2-tert-butyl-aminoethyl methacrylate, and 4-amino styrene, (b) carboxyl groups (e.g., those formed using acrylic acid, methacrylic acid, itaconic acid, sorbic acid, maleic acid, fumaric acid, and the like), (c) hydroxyl groups (e.g., those formed using hydroxyalkyl acylates and methacrylates such as hydroxyethyl acrylate, hydroxypropyl acrylate, hydroxyethyl methacrylate, and hydroxypropyl methacrylate, and hydroxystyrene), (d) isocyanate groups (e.g., those formed using vinyl isocyanate, isoprenyl isocyanate, isocyanatoalkyl acrylates or methacrylates such as 2-isocyanatoethyl acrylate or methacrylate, 3-isocyanatopropyl acrylate or methacrylate, 4-isocyanatobutyl acrylate or methacrylate, 6-isocyanatohexyl acrylate or methacrylate, 1-methyl-2-isocyanatoethyl methacrylate or 1,1-dimethyl-2-isocyanatoethyl methacrylate, stryrenic isocyanates such as styrene isocyanate and m-isopropenyl-α,α-dimethylbenzyl isocyanate), and (e) anhydride groups (e.g., those formed using acrylic and methacrylic acid anhydride, maleic anhydride and itaconic anhydride), among others.

Methods for preparing the polymers of interest would include those methods known for the production of polymers, for example, living cationic or anionic polymerization, as well as controlled free radical polymerization (CRP) methods such as nitroxide mediated polymerization (NMP), reversible addition-fragmentation chain transfer polymerization (RAFT), atom transfer radical polymerization (ATRP) and group transfer polymerization (GTP).

CRP methods such as ATRP and NMP are particularly well suited for block copolymer polymerization since they allow for the direct polymerization of functional monomers such as monomers containing carboxyl, amine, or hydroxyl groups, without the need to perform expensive and time consuming protections and de-protection reactions that are needed with ionic polymerization methods.

Once polymers are formed with the above or other reactive groups, bioactive species may be coupled to the same, for example, using linking agents. Specific examples of commonly used linking agents include glutaraldehyde, diisocyanates, diiosothiocyanates, bis(hydroxysuccinimide)esters, maleimidehydroxysuccinimide esters, carbodiimides, N,N'-carbonyidiimidazole imidoesters, and difluorobenzene derivatives, among others. One ordinarily skilled in the art will recognize that any number of other coupling agents may be used depending on the functional groups present. Functional groups present on the block copolymer or bioactive species may be converted, as desired, into other functional groups prior to reaction, e.g. to confer additional reactivity or selectivity. Further information on covalent coupling may be found, for example, in U.S. Pub. No. 2005/0002865.

As a specific example, an acrylate based triblock polymers may be prepared using NMP along with the SG1-type catalysts developed by ARKEMA by Atofina Chemicals. Such polymers may include rubbery midblocks composed of soft, low Tg polymer blocks, for example, poly(butyl acrylate) or poly(lauryl acrylate blocks, and hard endblocks composed of high Tg polymer blocks, for example, blocks of poly(methyl methacrylate), poly(styrene) or poly(isobornyl acrylate). By copolymerizing the monomers of either of the two phases, along with a monomer containing reactive groups such as carboxyl or amine groups (e.g., acrylic acid, among others), sites are provided for attachment of bioactive species (e.g., bioactive-peptide containing species, such as peptides consisting of or comprising an RGD sequence), for instance, using standard carbodiimide chemistry. The density of such reactive groups within the block copolymer may be varied by varying the monomer ratio between the reactive monomers and the low Tg monomers, or by varying the monomer ratio between the reactive monomers and the high Tg monomers, depending on which block the reactive monomer is to be introduced. Other reactive monomer species such as aminoethyl methacrylate or hydroxyethyl acrylate, among others (see above) may also be used to produce similar reactive polymers.

In some embodiments, on the other hand, the block copolymer of interest will inherently possess reactive groups through which bioactive species may be coupled, and thus will not require copolymerization with a reactive monomer. For example, an acrylate based triblock polymers may be prepared by NMP which include rubbery midblocks composed of low Tg polymer blocks, for example, poly(butyl acrylate) blocks, and hard end blocks composed of hydrophilic, high Tg polymer blocks, for example, blocks of poly (hydroxyethyl methacrylate). In addition to providing highly hydrophobic phase domains, the poly(hydroxyethyl methacrylate) blocks also contain hydroxyl groups to which bioactive species may be linked, to varying degrees of saturation.

In other embodiments, the bioactive species is incorporated at the time of polymer chain formation. For example, copolymerization may be conducted using a bioactive monomer, for instance, the reaction product of a reactive unsaturated monomer (e.g., one having a carboxyl, amino, hydroxyl, isocyanate, anhydride, etc. groups) and a bioactive species. Analogous to the copolymerization above, the density of the bioactive species within the block copolymer may be varied by varying the monomer ratio between the bioactive monomers and the low Tg monomers, or by varying the monomer ratio between the bioactive monomers and the high Tg monomers, depending on which block the bioactive monomer is to be introduced.

In other embodiments, the block copolymers of the present invention further include polymer blocks with biomimetic properties, for example, polymer blocks containing anionic sulfonate groups (e.g., sulfonated polystyrene blocks, among others), which have heparinoid activity, and blocks polymerized with methacryloxyethyl phosphoryl choline type monomers, which are known to yield cell membrane-like surfaces).

A variety of implantable or insertable medical devices may be provided with block copolymer regions, in accordance with the invention, including, for example, catheters (e.g., renal or vascular catheters), balloons, catheter shafts, guide wires, filters (e.g., vena cava filters), stents (including coronary vascular stents, cerebral, urethral, ureteral, biliary, tracheal, gastrointestinal and esophageal stents), stent grafts, vascular grafts, vascular access ports, embolization devices including cerebral aneurysm filler coils (including Guglilmi detachable coils and other metal coils), myocardial plugs, septal defect closure devices, patches, pacemakers and pacemaker leads, defibrillation leads and coils, left ventricular assist devices (LVADs), artificial hearts and pumps, total artificial hearts, heart valves, vascular valves, tissue engineering scaffolds for cartilage, bone, skin and other in vivo tissue regeneration, and so forth.

The block copolymers may be provided over the entire surface of the medical device or over only a portion of the medical device surface. For example, with tubular devices such as stents (which can comprise, for example, a laser cut or mechanically cut tube, one or more braided, woven, or knitted filaments, etc.), block copolymers may be provided over the entire surface of the stent, or they may be provided on the inner luminal surface of the stent, on the outer abluminal surface of the stent, and/or on the lateral surfaces between the luminal and abluminal surfaces (including the ends). The block copolymers may be provided in desired patterns, for instance, using appropriate masking techniques, among others. As another example, block copolymers may be provided over certain device components but not others.

Materials for use as underlying medical device substrates include (a) organic materials (e.g., materials' containing 50 wt % or more organic species) such as polymeric materials and (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., biostable metals such as gold, platinum, palladium, iridium, osmium, rhodium, titanium, tantalum, tungsten, and ruthenium, and bioresorbable metals such as magnesium) and metal alloys, including metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys).

Specific examples of organic materials may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-alkylene copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers and blends of the above.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising (a) a substrate and (b) a polymeric region disposed over said substrate, said polymeric region having a surface and comprising a block copolymer that comprises first and second polymer blocks, which correspond to first and second immiscible phase domains, respectively, within said polymeric region, wherein at least one of said first and second polymer blocks comprises a covalently attached first bioactive species, wherein said first block comprises a monomer selected from methyl methacrylate, styrene, vinyl naphthalene, isobornyl acrylate and combinations thereof, and wherein said second block comprises a monomer selected from butyl methacrylate, butyl acrylate, lauryl acrylate, isobutylene, ethylene oxide, hydroxyethyl methacrylate, hydroxyethyl acrylate, acrylic acid, methacrylic acid, hydroxstyrene, vinyl benzoic acid, and combinations thereof.

2. The medical device of claim 1, wherein at least one of said first and second phase domains has a surface dimension that averages between 10 and 500 nm.

3. The medical device of claim 1, wherein each of said first and second phase domains has a surface dimension that averages between 10 and 500 nm.

4. The medical device of claim 1, wherein at least one of said first and second phase domains has a surface dimension that averages between 10 and 200 nm.

5. The medical device of claim 1 comprising a polymer that contains a functional group that covalently bonds to the first bioactive species and which polymer comprises monomers having a functional group selected from (a) amine groups, (b) carboxyl groups, (c) hydroxyl groups, (d) isocyanate groups or (e) anhydride groups.

6. The medical device of claim 1 wherein the first bioactive species is selected from adhesive polysaccharide-containing species and adhesive peptide-containing species.

7. The medical device of claim 1, wherein said first bioactive species comprises a bioactive peptide sequence.

8. The medical device of claim 1, wherein said first bioactive species comprises a bioactive RGD or YIGSR peptide sequence.

9. The medical device of claim 1, wherein said first polymer block comprises said covalently attached first bioactive species and said second polymer block comprises a second covalently attached bioactive species which is different from the first covalently attached bioactive species.

10. The medical device of claim 9, wherein said second bioactive species is a glycosaminoglycan.

11. The medical device of claim 1, wherein said first bioactive species is attached at various points along one of said polymer blocks.

12. The medical device of claim 1, wherein said first bioactive species is attached at the end of one of said polymer blocks.

13. The medical device of claim 1 wherein the domain structures are approximately uniform.

14. The medical device of claim 1, wherein said block copolymer is a diblock copolymer.

15. The medical device of claim 1, wherein said first and second immiscible phase domains have a morphology selected from (i) cylinders of the first phase domain within the second phase domain, which cylinders have a vertical orientation relative to the surface of the polymeric region, (ii) lamellae of the first and second phase domains, which lamellae have a vertical orientation relative to the surface of the polymeric region, (iii) dual labyrinths of the first and second phase domains, and (iv) cylinders of the second phase domain within the first phase domain, which cylinders have a vertical orientation relative to the surface of the polymeric region.

16. The medical device of claim 1, wherein said first and second immiscible phase domains have a morphology comprising alternating lamellae of the first and second phase domains, which lamellae have a vertical orientation relative to the surface of the polymeric region.

17. The medical device of claim 1, wherein said block copolymer is a triblock copolymer comprising said first block as a central block and two of said second blocks as end blocks.

18. The medical device of claim 1, wherein said block copolymer further comprises a third polymer block corresponding to a third immiscible phase domain within said polymeric region.

19. The medical device of claim 18, wherein said third block is a biomimetic block.

20. The medical device of claim 19, wherein said biomimetic block is selected from polymer blocks that comprise anionic groups and polymer blocks that comprise monomers comprising one or more phosphoryl choline groups.

21. The medical device of claim 20, wherein said anionic groups comprise sulfonate groups.

22. The medical device of claim 1, wherein said polymeric region is formed by a rapid solidification technique.

23. The medical device of claim 1, wherein said polymeric region is formed by a process that comprises application of a field selected from an electric field, a magnetic field, a mechanical shear field and a solvent gradient field.

24. The medical device of claim 1, wherein said polymeric region is formed by a process that comprises an annealing step.

25. The medical device of claim 1, wherein said medical device is selected from a stent, a graft, a stent graft, a vena cava filter, an embolic coil, a heart valve, a left ventricular access device, and an artificial heart.

26. The medical device of claim 1, wherein said substrate is selected from a metallic substrate, a polymeric substrate and a ceramic substrate.

* * * * *

UNITED STATES PATENT AND TRADEMARK OFFICE
CERTIFICATE OF CORRECTION

PATENT NO. : 8,092,818 B2
APPLICATION NO. : 11/435799
DATED : January 10, 2012
INVENTOR(S) : Robert E. Richard and Michael N. Helmus It is certified that error appears in the above-identified patent and that said Letters Patent is hereby corrected as shown below:

Specification, col. 7, line 42, after "by" remove "increased by".

Specification, col. 7, line 47, after "substrate" change "is" to --has--.

Signed and Sealed this
Tenth Day of April, 2012

David J. Kappos
*Director of the United States Patent and Trademark Office*

SEQUENCE LISTING

```
<160> NUMBER OF SEQ ID NOS: 5

<210> SEQ ID NO 1
<211> LENGTH: 3
<212> TYPE: PRT
<213> ORGANISM: Artificial
<220> FEATURE:
<223> OTHER INFORMATION: Chemically synthesized

<400> SEQUENCE: 1

Arg Gly Asp
1

<210> SEQ ID NO 2
<211> LENGTH: 5
<212> TYPE: PRT
<213> ORGANISM: Artificial
<220> FEATURE:
<223> OTHER INFORMATION: Chemically synthesized

<400> SEQUENCE: 2

Tyr Gly Arg Gly Asp
1               5

<210> SEQ ID NO 3
<211> LENGTH: 4
<212> TYPE: PRT
<213> ORGANISM: Artificial
<220> FEATURE:
<223> OTHER INFORMATION: Chemically synthesized

<400> SEQUENCE: 3

Arg Glu Asp Val
1

<210> SEQ ID NO 4
<211> LENGTH: 5
<212> TYPE: PRT
<213> ORGANISM: Artificial
<220> FEATURE:
<223> OTHER INFORMATION: Chemically synthesized

<400> SEQUENCE: 4

Tyr Ile Ser Gly Arg
1               5
```

```
<210> SEQ ID NO 5
<211> LENGTH: 3
<212> TYPE: PRT
<213> ORGANISM: Artificial
<220> FEATURE:
<223> OTHER INFORMATION: Chemically synthesized

<400> SEQUENCE: 5

Asn Gly Arg
1
```